United States Patent
Kohler et al.

(10) Patent No.: US 6,520,966 B1
(45) Date of Patent: Feb. 18, 2003

(54) SETTING INSTRUMENT FOR A TIBIA PART OF A KNEE JOINT PROSTHESIS

(75) Inventors: Michael Kohler, Uster (CH); Thomas Trachsler, Winterthur (CH); Wolfgang Schwägerl, Vienna (AT); Nikolaus Böhler, Linz (AT)

(73) Assignee: Sulzer Orthopedics Ltd., Baar (CH)

( * ) Notice: Subject to any disclaimer, the term of this patent is extended or adjusted under 35 U.S.C. 154(b) by 142 days.

(21) Appl. No.: 09/665,889

(22) Filed: Sep. 20, 2000

(30) Foreign Application Priority Data

Sep. 21, 1999  (EP) .............................................. 99810841

(51) Int. Cl.[7] .............................. A61F 5/00; A61B 17/32
(52) U.S. Cl. .............................. 606/86; 606/80; 606/79; 606/87
(58) Field of Search ...................... 606/86, 80, 79, 606/81, 84, 88, 102, 170, 180, 167; 623/20.15, 20.32

(56) References Cited

U.S. PATENT DOCUMENTS

| | | | |
|---|---|---|---|
| 5,499,985 A | | 3/1996 | Hein |
| 5,499,986 A | | 3/1996 | Dimarco |
| 5,776,200 A | | 7/1998 | Johnson |
| 5,827,290 A | * | 10/1998 | Bradley ....................... 606/86 |
| 5,951,561 A | * | 9/1999 | Pepper et al. ................. 606/80 |
| 6,010,508 A | * | 1/2000 | Bradley ....................... 606/86 |
| 6,355,045 B1 | * | 3/2002 | Gundlapalli et al. .......... 606/88 |

FOREIGN PATENT DOCUMENTS

EP          0780090 A1    6/1997

* cited by examiner

Primary Examiner—John J. Wilson
Assistant Examiner—Robyn Kien Doan
(74) Attorney, Agent, or Firm—Townsend and Townsend and Crew LLP

(57) ABSTRACT

A setting instrument for a tibia part (1) of a knee joint prosthesis comprises a separate attachment piece (2) for the securing at the tibia part (1) and comprises a hand piece (3) which can be brought firmly into engagement with the separate attachment piece (2).

11 Claims, 3 Drawing Sheets

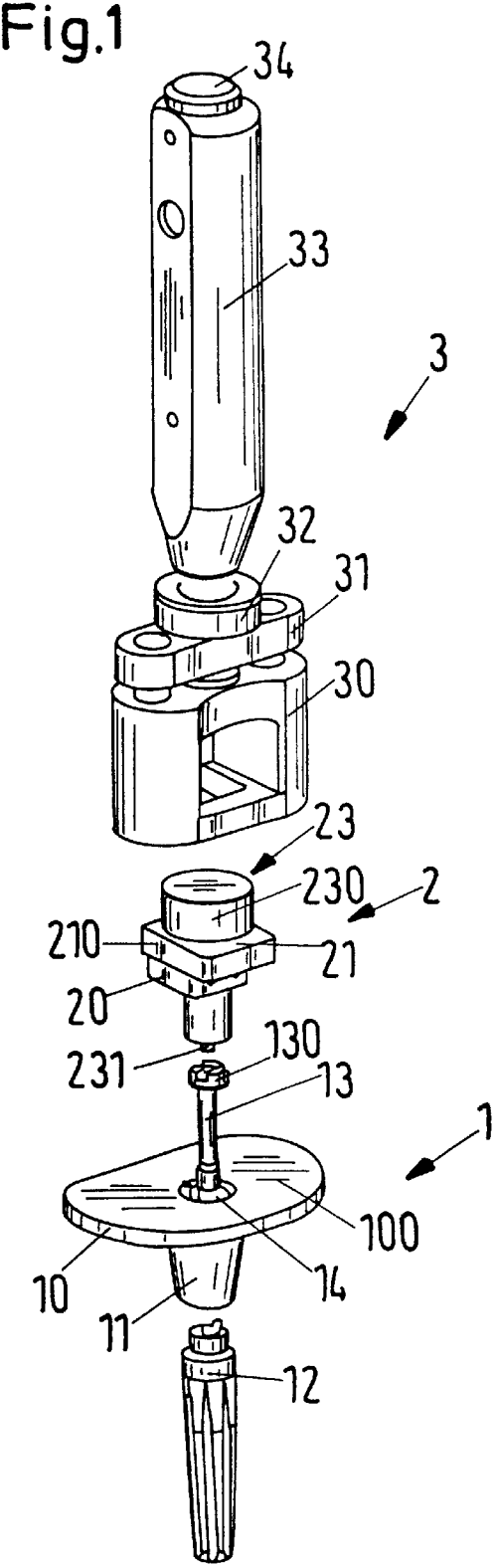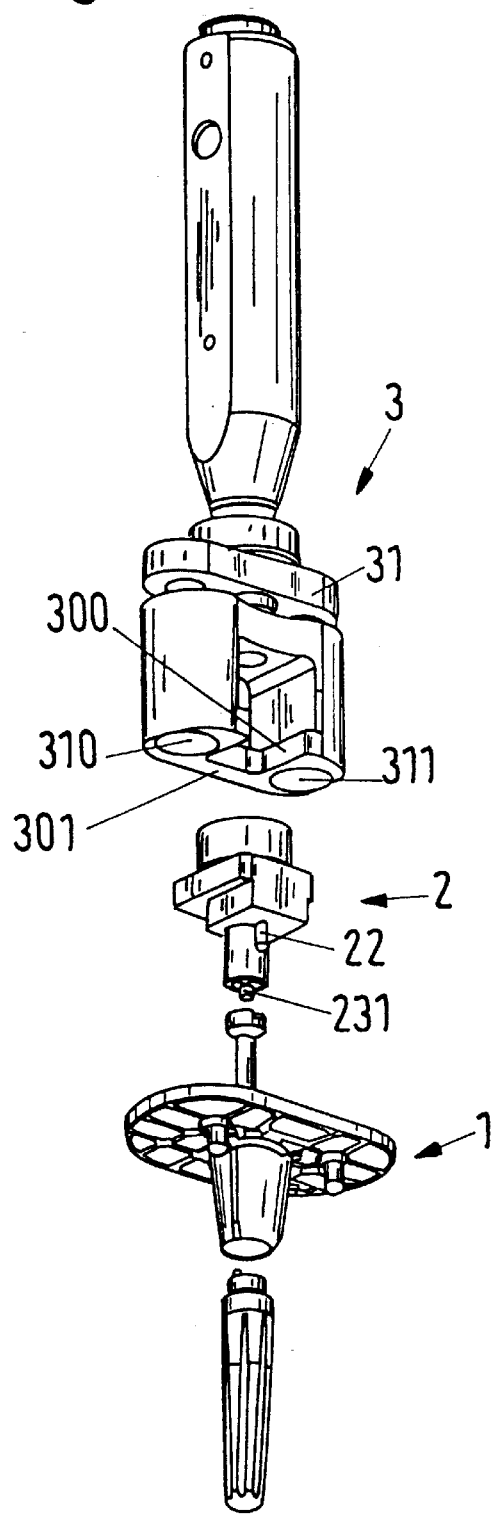

Figure 4:
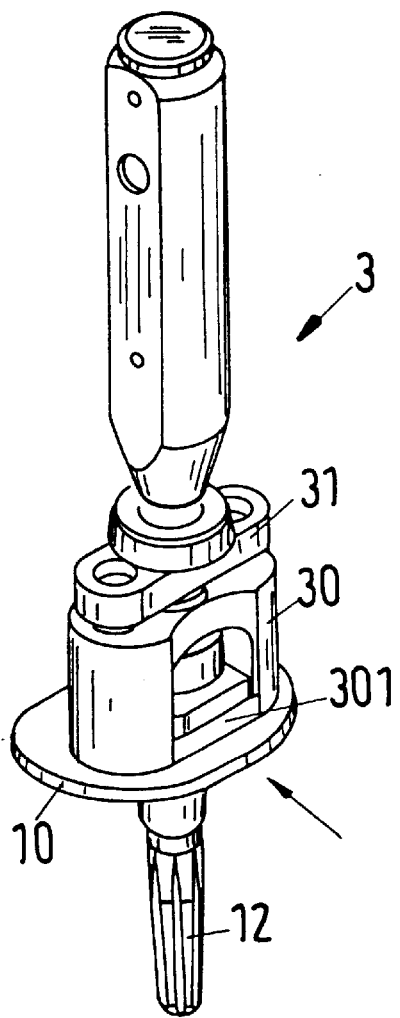

Fig.3
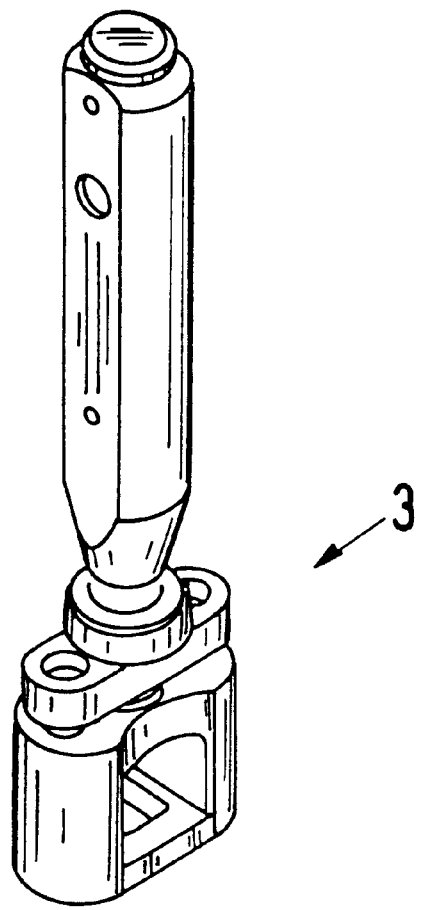
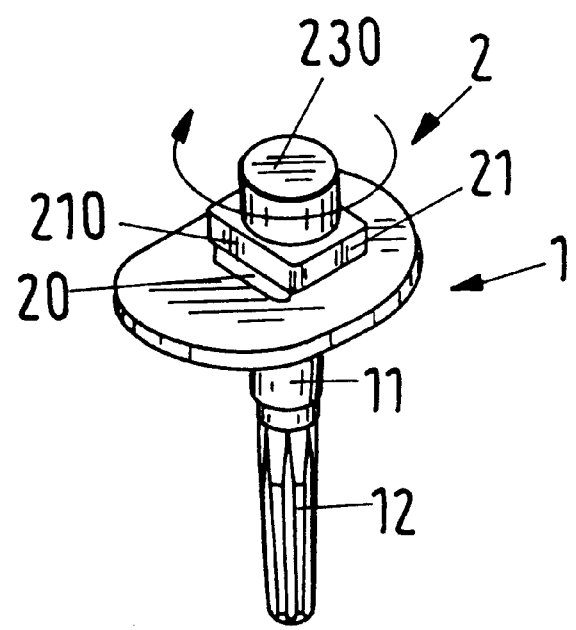

SETTING INSTRUMENT FOR A TIBIA PART OF A KNEE JOINT PROSTHESIS

The invention relates to a setting instrument for a tibia part of a knee joint prosthesis.

Knee joint prostheses typically comprise a tibia part which is secured to the tibia and a femur part which is secured to the femur. The tibia part and the femur part are regularly formed metallically. A bearing body with bearing surfaces which is typically manufactured of plastic, e.g. of polyethylene, is arranged between the condylary articulation surfaces of the femur part and the surface of the tibia part which points away from the tibia to the femur. The condulary articulation surfaces of the femur part slide on the bearing surfaces of the bearing body.

In the implantation of a knee joint prosthesis after the surgical opening of the knee the tibia and the femur are prepared with the help of corresponding gauges in such a manner that after the preparation is complete the corresponding prosthesis parts, namely the tibia part on the one hand and the femur part on the other hand, can be secured at the tibia and the femur respectively.

The implantation of the tibia part previously typically takes place in such a manner that orthopedist pre-positions or lightly fixes respectively the tibia part on the prepared tibia by hand and then drives in the tibia stem or a tibia shaft which is connected to the tibia stem further into the prepared tibia. This further driving in typically takes place with the help of an instrument which is placed onto the surface of the tibia part which faces the femur, but which is not fixed there however. Through blows onto the proximal end of this instrument then the tibia stem or a tibia shaft which is connected to the tibia stem respectively is driven into the tibia until the tibia part is secured in the desired manner at the tibia.

This kind of implantation of the tibia part is however rather inconvenient for the orthopedist from the point of view of the handling. He must first pre-position the tibia part by hand on the prepared tibia and then drive the tibia stem or the tibia shaft which is connected to the tibia stem respectively further into the tibia with a not definitively fixable instrument. In this there is the danger in the pre-positioning that the tibia part slips out of the hand of the orthopedist or of another member of the operating personnel and as a result can no longer be used in this operation for reasons of sterility. In the event of a non-central placing on of the instrument during the driving in of an already pre-positioned tibia part an undesirable tipping or skewing of the tibia part can occur, which must be correspondingly corrected in the further driving in.

Here the invention wishes to provide a remedy. In particular it is an object of the invention to avoid the above named disadvantages and to place an instrument in the hands of the orthopedist which facilitates the handling for him during the implantation.

This object is satisfied by a setting instrument such as is characterized by the features of the independent patent claim. Particularly advantageous designs of the instrument result from the features of the subordinate claims.

In particular, this object is satisfied by a setting instrument for a tibia part of a knee joint prosthesis comprising a separate attachment piece for the securing at the tibia part and comprising a hand piece which can be brought firmly into engagement with the separate attachment piece.

Thus prior to the implantation of the tibia part the attachment piece is first secured to the tibia part and then the hand piece is brought firmly into engagement with the attachment piece. This arrangement consisting of a tibia part, an attachment piece and a hand piece then forms a unit which is firmly connected together and which the orthopedist can handle very conveniently. The arrangement is very easy for the orthopedist to grip at the hand piece, so that the danger that the tibia part slips away from the orthopedist or other operating personnel is extremely low. Furthermore, as a result of its good handling ability for the orthopedist the setting instrument permits a precise pre-positioning of the tibia part. Once the tibia part is pre-positioned, the arrangement consisting of the tibia part, the attachment piece and the hand piece can then remain firmly connected together and the orthopedist can—where appropriate after checking the pre-positioning—drive the tibia stem or a tibia shaft which is connected to the tibia stem respectively further into the tibia without having to change the instrument in so doing. He exerts, e.g. with a suitable hammer, blows onto the proximal end of the hand piece, through which the tibia stem or a tibia shaft which is connected to it respectively is driven further into the tibia. The handling is thereby simple and convenient for the orthopedist. Furthermore, both the attachment piece and the hand piece can be simply and reliably sterilized. Moreover, a well defined introduction of the forces into the tibia part also takes place during the driving in.

In one exemplary embodiment of the setting instrument the hand piece and the attachment piece are designed in such a manner that in the secured state they come to lie within the region which is bounded by that surface of the tibia part which points away from the tibia and towards the femur. Thus in this exemplary embodiment no instrument parts protrude beyond the "outer contours" of the tibia part in the assembled state. This is particularly advantageous for the implantation since namely the surgical opening of the knee should remain as small as possible, on the other hand however, instrument parts which project beyond the (maximum outer) dimensions could come into conflict during the implanting with soft parts etc. which are arranged around the tibia and could hinder the implantation.

In a further exemplary embodiment the attachment piece has a support part which when the attachment piece is secured lies in contact on that surface of the tibia part which points away from the tibia and towards the femur as well as a application part which is arranged proximally to the support part and can be brought into engagement with the hand piece. One could also say that the attachment piece lies on the bearing surface of the tibia part and has moreover a application part which is arranged proximally to this attachment piece, that the lying in contact on the tibia part and the engagement with the hand piece are thus separate from one another.

In a further development the application part of the attachment piece protrudes beyond the support part when considered in regard to its lateral dimensions, so that a projection is formed. The hand piece is provided at its distal end with a cut-out which receives the support part of the attachment piece during the engagement of the hand piece and the attachment piece and in so doing grips under the projection. This further development enables, after the securing of the attachment piece to the tibia part, a simple pushing on of the hand piece, which then grips under the projection. Through a subsequent bracing of the hand piece with the attachment piece the above described firmly connected together unit consisting of the tibia part, the attachment piece and the hand piece, which is easy for the orthopedist to handle, can be produced in a simple manner. This unit, which is easy for the orthopedist to handle, can for example also be assembled by other operating personnel.

In a further development the hand piece is provided with an abutment which limits the pushing on of the hand piece in the direction of the cut-out during the engagement of the hand piece and the attachment piece. Through this it is prevented that the hand piece can be pushed too far below the projection. For example a correspondingly arranged connection web can be provided as an abutment.

In a further exemplary embodiment of the setting instrument, means for the screwing of the attachment piece to the tibia part are provided for securing the attachment piece to the tibia part. For this, corresponding means (e.g. a thread) must naturally be provided at the tibia part. This kind of securing is not very complicated and expensive and is also simple to carry out as regards the handling.

In a further exemplary embodiment the hand piece has an engagement part at its distal end and proximally to the engagement part a pressure plate which can be displaced in the direction towards the engagement part or away from the latter respectively. The pressure plate is provided with pressure pieces which are firmly connected to the pressure plate and are arranged in the corresponding passage bores in the engagement part of the hand piece. During the displacement of the pressure plate in the direction towards the engagement part the pressure pieces emerge from the passage bores at the distal end and, respectively, during the displacement of the pressure plate they slide in the direction away from the engagement part into the passage bores. Thus for the firm engagement of the hand piece with the attachment piece which is secured to the tibia part the pressure plate is moved in the direction towards the engagement part, which takes place in that the pressure pieces emerge at the distal end from the bores and are braced on the bearing surface of the tibia part. Through this the engagement part is lifted off from the bearing surface of the tibia part and engages firmly under the projection at the attachment piece, through which a firm arrangement consisting of the tibia part, the attachment piece and the hand piece is formed. After the driving in of the tibia part the pressure piece is again moved away from the engagement part, with the pressure pieces sliding back into the bores in the engagement part and the engagement part again coming to lie on the tibia bearing surface and engaging only loosely under the projection, so that the hand piece can be removed again. Then the attachment piece is removed from the tibia part and the implantation of the tibia part is complete. This exemplary embodiment is simple both as regards the constructional cost and complexity and as regards the handling.

In order to drive in the tibia part a striking surface can be provided at the proximal end of the hand piece. Striking impulses can be exerted onto this striking surface with a suitable instrument, for example with a hammer, in order to drive the tibia stem or a shaft which is connected to the tibia stem respectively into the tibia.

Figure 5:
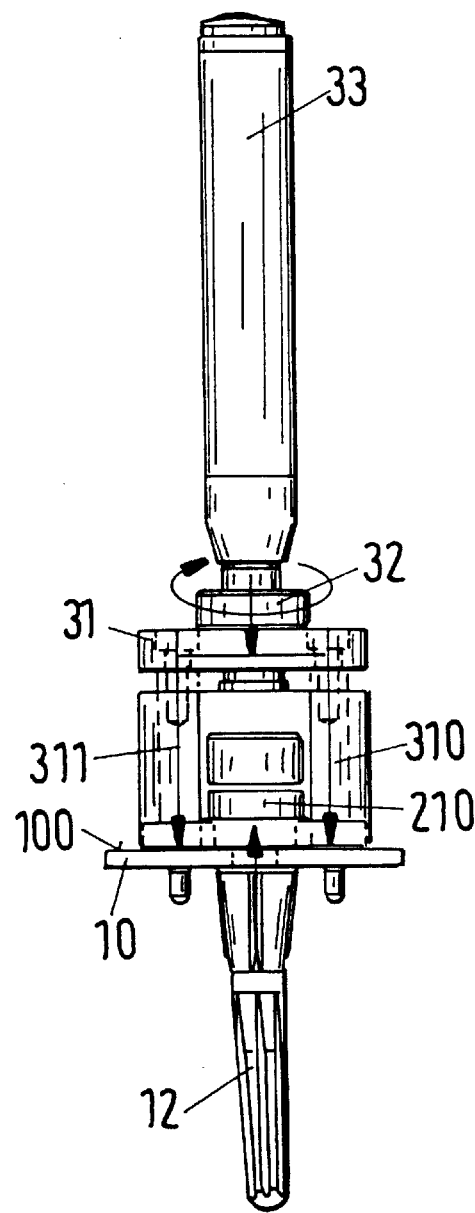

The invention will be explained in more detail in the following with reference to the drawings; in this in schematic illustration represents:

FIG. 1 an exploded view of the individual components: tibia part with tibia stem, shaft for accommodation in the tibia stem, waisted bolt for connecting the shaft and the tibia stem, attachment piece and hand piece, FIG. 2 the exploded view of FIG. 1, but from another perspective, however, FIG. 3 a tibia part with a tibia shaft which is already secured to the tibia stem and with an attachment piece which is secured to the tibia part on the one hand and the hand piece on the other hand, FIG. 4 a completely assembled arrangement comprising a tibia part with a tibia shaft which is already secured to the tibia stem, with an attachment piece which is secured to the tibia part and with a hand piece which is in firm engagement with the attachment piece and FIG. 5 the completely assembled arrangement of FIG. 4 in another view.

In the exploded view of FIG. 1 one recognizes a tibia part 1, which comprises here a tibia plateau 10 with a tibia stem 11, as well as a tibia shaft 12 which connects with the help of a waisted bolt 13, which passes through a bore 14, the tibia shaft 12 to the tibia stem 11 and thus to the tibia plateau 10. A thread is provided in the head 130 of the waisted bolt 13, the function of which will be discussed in more detail below.

Furthermore, one recognizes in FIG. 1 an attachment piece 2 which can be secured to the tibia part 1. The attachment piece 2 has a support part 20 which in the secured state lies in contact on the bearing surface 100 of the tibia plateau 10. Furthermore, the attachment piece 2 has a application part 21 which is arranged proximally to the support part 20 and protrudes beyond the support part 20 in regard to its lateral dimensions. Through this a projection 210 is formed, the function of which will be explained below. Furthermore, one recognizes in FIG. 2 that the attachment piece 2 has a rotational securing in the form of a pin 22 which projects downwardly from the support part 20 and which engages into a corresponding cut-out in the bore 14 in the tibia part 1. Finally, the attachment piece 2 also has a screw 23 which has a screw head 230 for operating the screw 23 and a threaded shaft 231 which protrudes outwardly at the lower end of the attachment piece 2. This threaded shaft 231 is provided in order to engage into the thread in the head 130 of the waisted bolt 13.

Finally, one also recognizes in FIG. 1 a hand piece 3 which comprises an engagement part 30 at its distal end and proximally to it a pressure plate 31, and furthermore an adjusting screw 32 as well as a hand grip 33, at the proximal end of which a striking surface 34 is provided. Restoring springs (not illustrated) are arranged between the engagement part 30 and the pressure plate 31. The pressure plate 31 can be displaced with the help of the adjusting screw 32 in the direction towards the engagement part 31 or in the direction away from the engagement part 31 respectively. The pressure plate is provided with two pressure pieces 310 and 311 (FIG. 2) which are firmly connected to the pressure plate 31 (e.g. are screwed to the latter, see FIG. 5).

In FIG. 2 one also recognizes that the engagement part 30 has a cut-out 300 at its distal end which is closed at one side by a web 301 which extends transversely to the cut-out. The web 301 forms an abutment in this situation, as will be explained in the following in the description of the method of functioning of the instrument.

The method of functioning is as follows: When the tibia shaft 12 is secured at the tibia plateau 10 (a tibia shaft 12 is not required in every implantation, in particular wherever possible not in first implantations, but is regularly used especially in re-operations or in the event of poor bone constitution) the attachment piece 2 is secured at the tibia part 1 in that through rotation of the screw head 230 (see the arrow in FIG. 3) the threaded shaft 231 (FIG. 2) is screwed into the thread in the head 130 (FIG. 1) of the waisted bolt 13. Alternatively, a thread is provided in the tibia stem 11 for the case that no tibia shaft 12 is required, and the threaded shaft 231 of the screw 23 is then formed correspondingly thicker, because it is then screwed directly into the tissue in the tibia stem 11, since of course no waisted bolt 13 is required. The pin 22 (FIG. 2) prevents the attachment piece 2 from being able to rotate during the screw connecting.

Once the attachment piece 2 is screwed to the tibia part 1 (FIG. 3), then the hand piece 3 with its engagement part 30 is pushed on in such a manner (see the arrow in FIG. 4) that the reception 300 (see FIG. 2) receives the support part 20 of the attachment piece 2 and engages loosely under the overhanging projection 210 which is formed by the application part 21 of the attachment piece 2. In this the pushing on of the hand piece 3 takes place until the web 301 (see FIG. 2) abuts at the support part 20 (see FIG. 4); the web 301 thus forms an abutment for the pushing on of the hand piece 3 or for its engagement part 30 respectively.

Once the hand piece 3 or its engagement part 30 is completely pushed on (FIG. 4), then it engages—as already mentioned—loosely under the projection 210 of the attachment piece 2, but is however not yet firmly connected to the latter. Now the adjusting screw 32 is actuated, through which the pressure plate 31 is moved with the pressure pieces 310 and 311 which are secured thereto in the direction towards the tibia plateau 10 (see the arrows in FIG. 5). As a result the pressure pieces 310 and 311 emerge at the distal end from the bores in the engagement part 30 (see the arrows in FIG. 5) and are braced on the tibia plateau 10 or, stated more precisely, on the bearing surface 100 of the tibia plateau 10. The pressure pieces 310 and 311 are firmly connected to the pressure plate 31; they are for example—as is indicated in FIG. 5—screwed to the pressure plate 31. On the other hand the engagement part 30 is immovably connected to the hand grip 33 or to the shaft respectively, along which the displacement screw 32 can be displaced. Through the displacing of the pressure plate 31 in the direction towards the engagement part 30 and the emerging of the pressure pieces 310 and 311 at the distal end of the engagement part 30 which takes place thereby, the engagement part 30 is thus drawn upwards (see the arrow in FIG. 5) and grips firmly under the projection 210 (see FIG. 2) which is formed by the application part 21 of the attachment piece 2. Through this a firm connection of the hand piece 3, the attachment piece 2 and the tibia part 1 comes into being.

These actions need not be performed by the orthopedist himself, but can for example be performed by other operating personnel who are present at the operation. The firmly connected together arrangement consisting of the hand piece 3, the attachment piece 2 and the tibia part 1 which is shown in FIG. 5 can then be handed to the orthopedist for the implantation. The orthopedist takes over the latter and then has a simple to handle arrangement which is reliably connected together in his hands.

Once the tibia part 1 is implanted, then the adjusting screw 23 is displaced in such a manner that the pressure plate 31 again moves in the direction away from the engagement part 30. Then the restoring springs (not illustrated) press the engagement part 30 away from the pressure piece 31, through which the pressure pieces 310 and 311 slide back into the bores in the engagement part 30. Through this the firm engagement of the hand piece 3 and the attachment piece 2 is released again and the hand piece 3 can be removed, cleaned and sterilized. Then the attachment piece 2 can be screwed off from the tibia part 1 (through rotation of the screw head 230) and the implantation of the tibia part 1 is complete.

What is claimed is:

1. Setting instrument for a tibia part of a knee joint prosthesis, comprising a separate attachment piece for the securing at the tibia part and comprising a hand piece which can be brought firmly into engagement with the separate attachment piece, the attachment piece having a support part which, when the attachment piece is secured, lies in contact on a surface of the tibia part which points away from the tibia and towards the femur, and an application part which is arranged proximally to the support part and can be brought into engagement with the hand piece, the application part of the attachment piece protruding beyond the support part when considered in regard to its lateral dimensions, so that a projection is formed, and the hand piece being provided at its distal end with a cut-out which receives the support part of the attachment piece during the engagement of the hand piece and the attachment piece and in so doing grips under the projection.

2. Setting instrument in accordance with claim 1, in which the hand piece and the attachment piece are designed in such a manner that in the secured state they come to lie within the region which is bounded by that surface of the tibia part which points away from the tibia and towards the femur.

3. Setting instrument in accordance with claim 1, in which the attachment piece has a support part which, when the attachment piece is secured, lies in contact on a surface of the tibia part which points away from the tibia and towards the femur, and an application part which is arranged proximally to the support part and can be brought into engagement with the hand piece.

4. Setting instrument in accordance with claim 3, in which the application part of the attachment piece protrudes beyond the support part when considered in regard to its lateral dimensions, so that a projection is formed, and in which the hand piece is provided at its distal end with a cut-out which receives the support part of the attachment piece during the engagement of the hand piece and the attachment piece and in so doing grips under the projection.

5. Setting instrument in accordance with claim 4, in which the hand piece is provided with an abutment which limits the pushing on of the hand piece in the direction of the cut-out during the engagement of the hand piece and the attachment piece.

6. Setting instrument in accordance with claim 1, in which means for the screwing of the attachment piece to the tibia part are provided for securing the attachment piece at the tibia part.

7. Setting instrument in accordance with claim 1, in which the hand piece has an engagement part at its distal end and, proximally to the engagement part, a pressure plate which can be displaced in the direction towards and away from the engagement part respectively, with the pressure plate being provided with pressure pieces which are firmly connected to the pressure plate and are arranged in corresponding passage bores in the engagement part of the hand piece, so that the pressure pieces emerge at the distal end from the passage bores during the adjusting of the pressure plate in the direction towards the engagement part and, respectively, slide into the passage bores during the displacement of pressure plate in the direction away from the engagement part.

8. Setting instrument in accordance with claim 1, in which a striking surface is provided at the proximal end of the hand piece.

9. Setting instrument for a tibia part of a knee joint prosthesis, comprising a separate attachment piece for the securing at the tibia part and comprising a hand piece which can be brought firmly into engagement with the separate attachment piece, and means for the screwing of the attachment piece to the tibia part to thereby secure the attachment piece at the tibia part.

10. Setting instrument for a tibia part of a knee joint prosthesis, comprising a separate attachment piece for the securing at the tibia part and comprising a hand piece which can be brought firmly into engagement with the separate attachment piece, the hand piece including an engagement part at its distal end and, proximally to the engagement part, a pressure plate which can be displaced in a direction towards and away from the engagement part respectively, the pressure plate being provided with pressure pieces which are firmly connected to the pressure plate and are arranged in corresponding passage bores in the engagement part of the hand piece, so that the pressure pieces emerge at the distal end from the passage bores during the adjusting of the pressure plate in the direction towards the engagement part and, respectively, slide into the passage bores during the displacement of the pressure plate in the direction away from the engagement part.

11. Setting instrument for a tibia part of a knee joint prosthesis, comprising a separate attachment piece for the securing at the tibia part, a hand piece which can be brought firmly into engagement with the separate attachment piece, and a striking surface at the proximal end of the hand piece.

* * * * *